United States Patent
Wang

(10) Patent No.: US 11,337,775 B2
(45) Date of Patent: May 24, 2022

(54) CHECK-DIRECTION PIN AND GUIDE TAP DRILL KIT FOR IMPLANTING A FIXTURE OF IMPLANT

(71) Applicant: WANG, Je Won, Daejeon (KR)

(72) Inventor: Je Won Wang, Daejeon (KR)

(73) Assignee: Je Won Wang, Daejeon (KR)

( * ) Notice: Subject to any disclaimer, the term of this patent is extended or adjusted under 35 U.S.C. 154(b) by 33 days.

(21) Appl. No.: 16/335,701

(22) PCT Filed: Dec. 14, 2018

(86) PCT No.: PCT/KR2018/015924
§ 371 (c)(1),
(2) Date: Mar. 22, 2019

(87) PCT Pub. No.: WO2019/124887
PCT Pub. Date: Jun. 27, 2019

(65) Prior Publication Data
US 2021/0338375 A1    Nov. 4, 2021

(30) Foreign Application Priority Data

Dec. 22, 2017 (KR) .......................... 10-2017-0177900

(51) Int. Cl.
*A61C 1/08* (2006.01)
*A61C 8/00* (2006.01)

(52) U.S. Cl.
CPC ............ *A61C 1/084* (2013.01); *A61C 8/0089* (2013.01)

(58) Field of Classification Search
CPC ......... A61C 1/082; A61C 1/084; A61C 1/085; A61C 8/0089; A61C 8/009; A61C 8/0092;
(Continued)

(56) References Cited

U.S. PATENT DOCUMENTS 5,320,529 A    6/1994 Weitzman
5,743,916 A *  4/1998 Greenberg ............. A61B 17/02
                                                     606/102
(Continued)

FOREIGN PATENT DOCUMENTS

CN    102869313    1/2013
CN    102892379    1/2013
(Continued)

OTHER PUBLICATIONS

SIPO, Office Action of CN 201880069353.3 dated Feb. 26, 2021.
(Continued)

*Primary Examiner* — Jacqueline T Johanas
*Assistant Examiner* — Holly T. To
(74) *Attorney, Agent, or Firm* — Lex IP Meister, PLLC

(57) ABSTRACT

A direction checking pin and a guide tap drill kit for insertion of a fixture for an implant includes an endosseous fixing guide, a direction checking pin body and a guide tap drill. The endosseous fixing guide and the direction checking pin body are combined and then inserted into an already-formed insertion hole and only the direction checking pin body is removed after checking a direction of the insertion hole, and the guide tap drill is inserted to the endosseous fixing guide remaining in the insertion hole and then rotated so as to enter into the insertion hole such that a screw thread is formed in accordance with the direction of the insertion hole at an inner wall of the insertion hole by the tap drill.

6 Claims, 8 Drawing Sheets

(58) Field of Classification Search
CPC ... A61B 17/17; A61B 17/176; A61B 17/1633; A61B 17/1655; A61B 17/1673
USPC .................................................. 433/75
See application file for complete search history.

(56) References Cited

U.S. PATENT DOCUMENTS

| | | | |
|---|---|---|---|
| 6,179,615 | B1 | 1/2001 | Blacklock |
| 7,845,943 | B2 * | 12/2010 | Meitner .................. A61C 1/084 |
| | | | 433/75 |
| 9,283,057 | B2 | 3/2016 | Sanders |
| 10,973,607 | B2 * | 4/2021 | Dolfi ...................... A61C 1/085 |
| 2007/0111156 | A1 | 5/2007 | Gittelson |
| 2009/0291414 | A1 * | 11/2009 | Wang .................... A61C 8/005 |
| | | | 433/174 |
| 2011/0045437 | A1 * | 2/2011 | Ami ..................... A61C 8/0022 |
| | | | 433/174 |
| 2012/0135373 | A1 * | 5/2012 | Cheng .................... A61B 6/14 |
| | | | 433/75 |
| 2013/0004916 | A1 * | 1/2013 | Bellanca ............. A61C 8/0068 |
| | | | 433/173 |
| 2013/0122456 | A1 * | 5/2013 | Takebayashi ........ A61C 8/0089 |
| | | | 433/75 |
| 2015/0150656 | A1 * | 6/2015 | Suter ................... A61C 8/0089 |
| | | | 433/75 |
| 2016/0015483 | A1 | 1/2016 | Kumar et al. |

FOREIGN PATENT DOCUMENTS

| | | | | |
|---|---|---|---|---|
| CN | 204364147 | | 6/2015 | |
| CN | 104814786 | | 8/2015 | |
| CN | 105411696 | | 3/2016 | |
| CN | 106923919 | | 7/2017 | |
| DE | 102009031692 | | 12/2010 | |
| EP | 0328911 | | 8/1989 | |
| EP | 2292175 | | 3/2011 | |
| EP | 2276417 | | 7/2018 | |
| GB | 1419273 | | 12/1975 | |
| JP | 2007-515198 | | 6/2007 | |
| JP | 2012-501768 | | 1/2012 | |
| JP | 2013-503664 | | 2/2013 | |
| JP | 2013-126525 | | 6/2013 | |
| KR | 20090053970 A | * | 5/2009 | .......... A61B 17/1673 |
| KR | 10-2009-0111978 | | 10/2009 | |
| KR | 10-2009-0112385 | | 10/2009 | |
| KR | 10-2010-0034447 | | 4/2010 | |
| KR | 10-2016-0104373 | | 9/2016 | |
| KR | 10-1705871 | | 2/2017 | |
| KR | 10-1841747 | | 3/2018 | |
| RU | 2339336 | | 11/2008 | |
| WO | WO-9521590 A1 | * | 8/1995 | ........... A61C 8/0089 |
| WO | WO-2004098435 A2 | * | 11/2004 | ............. A61C 1/084 |
| WO | WO-2007129955 A1 | * | 11/2007 | ............. A61C 8/009 |
| WO | WO-2009117208 A1 | * | 9/2009 | ........... A61F 2/2803 |
| WO | WO-2014108906 A1 | * | 7/2014 | ........... A61C 8/0089 |

OTHER PUBLICATIONS

EPO, European Search Report of EP 18892772.7 dated Aug. 13, 2021.

Rospatent, Notice of Allowance of RU 2020114775 dated Nov. 20, 2020.

* cited by examiner

20

(a) : straight lined, inclined (partial penetration)
(b) : straight lined, inclined (full penetration)
(c) : entirely inclined
(d) : iteration of inclined portion and straight lined portion
(e) : iteration of straight lined portion and inclined portion
(f) : entirely straight lined (a)   (b)

(c)   (d)   (e)   (f)

(the entire bone cutting portion)

(partial bone cutting portion)

CHECK-DIRECTION PIN AND GUIDE TAP DRILL KIT FOR IMPLANTING A FIXTURE OF IMPLANT

TECHNICAL FIELD

The present invention relates to a direction checking pin and a tap drill kit for inserting a fixture of an implant in a direction of an insertion hole.

Specifically, the present invention relates to a package kit for forming a female screw thread that can guide a screw thread of a fixture for an implant in an inner wall of an insertion hole by forming the insertion hole to which a fixture is implanted in an alveolar bone by using a drill, fitting a direction checking pin into the insertion hole to check whether a direction of the insertion hole is properly set, and screwing a tap drill along the direction check pin remaining in the insertion hole.

Conventionally, the implant fixture is manually inserted after the insertion hole is formed and thus a direction of the already-formed insertion hole and an implant direction of the fixture cannot match without help of a specifically designed tool even by a skilled operator (physician), and thus the alveolar bone at the inner wall of the insertion hole cannot be prevented from being damaged.

Accordingly, the present invention relates to a package kit that can implant a fixture for an implant by forming the female screw in the inner wall of the insertion hole in a direction that precisely matches a direction of the insertion hole to accurately guide an implant direction of the fixture, thereby preventing damage to the alveolar bone in the inner wall of the insertion hole.

Conventionally, in order to form the female screw in the inner wall of the insertion hole by screwing the tap drill in a direction of the insertion hole, as shown in ① of FIG. 6, a guide bar 100 having a diameter that is the same as that of the insertion hole is formed at an end of the tap drill such that the female screw is formed at the inner wall of the insertion hole in a direction that matches the insertion hole direction as the guide bar 100 enters along the implant hole. Thus, the diameter of the insertion hole, which is formed in the shape of a cylinder, should be constant. However, as shown in ③ and ④ of FIG. 6, since most of the fixtures for the implant are inclined at difference diameters from the upper and lower portions, the insertion direction cannot be guided by the guide rod of the tap drill, and thus a tap drill having the guide rod 100, which is provided in accordance with the already-formed insertion hole, cannot be used.

Thus, in case of the insertion hole, which is inclined as shown in ③ and ④ of FIG. 6, a general tap drill from which the guide rod 100 is removed does not include a device that can guide in the insertion direction, and thus even a well-skilled operator (doctor) cannot form a female screw at an inner wall of the insertion hole in a direction exactly matching the direction of the insertion hole with a tap drill without a device capable of guiding it.

BACKGROUND ART

A fixture, which is an artificial root of a tooth used in dental implant surgery, is small in size and should be hygienically stored, and thus it is generally stored in a so-called ample type container.

Thus, in order to insert the fixture into an alveolar bone, the fixture needs to be picked up from the ample type container, located on a hole pre-drilled at the alveolar bone of a patient, and inserted into the hole using an additional tool with application of a proper torque to the fixture.

Meanwhile, in general, the fixture needs to be inserted in accordance with a direction of an insertion hole formed in the alveolar bone to minimize damage to the alveolar bone at an inner wall of the insertion hole, but the fixture is inserted in a direction of the already-formed insertion hole only depending on an operator's memory (dentist's memory) and thus is it actually difficult to insert the fixture in the insertion hole in accordance with the direction of the insertion hole, which has been already formed.

Accordingly, when a female screw is formed at an inner wall of the insertion hole in accordance with the direction of the insertion hole formed in the alveolar bone before insertion of the fixture, a screw thread of the fixture can be inserted along the female screw at the inner wall of the insertion hole and thus can be inserted in accordance with the direction of the already-formed insertion hole, and thus the applicant determined to provide an apparatus that can check a direction of an insertion hole and guide a use direction of a tap drill so as to form the female screw at the inner wall of the insertion hole according to the checked direction. However, since the fixture has an inclined shape, the tap drill cannot be used in accordance with the direction of the insertion hole, and thus methods for inserting multiple fixtures in parallel with each other rather than using the tap drill have been researched and developed.

As a related art, Patent Registration No. 10-1573466 discloses a parallel insertion device for dental implants and a method for parallel insertion of an implant.

The above-stated method relates to an apparatus for parallel insertion of dental implants and a method for parallel insertion of implants, wherein a connector is provided for supporting the parallel insertion of the implant at various positions such as above the gums, below the gums, and the like, and wherein the implant treatment can be carried out in various forms.

For realization of this, an apparatus including: a fixture 10 to which a drill hole 1a formed in an alveolar bone 1 of a patient is combined in a manner of insertion, and in which a connector receiving groove 12 that is opened upwardly is formed; a connector 20 provided with receiving holes 21 that are received in receiving grooves 11 respectively formed in a plurality of fixtures 10 at opposite sides thereof, wherein a plurality of artificial tooth fastening grooves 22 that are opened to the upper side for combination with an artificial tooth 40 and connected with each other are provided in the receiving hole 21 and wherein a screw fastening hole 23 is formed at a lower portion of the connector 20, while penetrating therethrough; and a fastening screw 30 that is screw-fastened to the screw fastening hole 23 such that the receiving hole 21 of the connector can be fixed to the fixture 10, is disclosed.

As another method, Patent Registration No. 10-1291754 discloses a parallel insertion device for dental implants and a method for parallel insertion of an implant.

The above-stated method relates to an apparatus for parallel implantation of dental implants and a method of inserting the same using dental implants, and to improve the stability of implant treatment for edentulous patients and to shorten the time for manufacturing the prosthesis.

For realization of this, an apparatus of which two horizontal supports 10 are connected with each other by a mutual joint rod 20 at opposite sides of the mutual joint rod 20 in a symmetric manner, wherein a plurality of horizontal guide holes 11 that horizontally balance the implant, an anchor screw hole 12 that fastens an anchor screw 13, and a connection hole 14 that is combined with a connection screw 15 for connection with an implant connector 30 are respectively formed in each of the horizontal supports 10.

The two methods are commonly used to improve the technical stability of the edentulous patient, and have a structure that is not applicable to one implant treatment, and directions of multiple insertion holes are parallel to each other and damage to alveolar bone in an inner wall of the insertion hole cannot be fully prevented when the fixture is implanted.

As another method, Registered Patent No. 10-1763763 discloses an apparatus for guiding an implant location.

The above-disclosed method provides an apparatus for guiding a position in an alveolar bone in an implant treatment and has a width and height equal to or smaller than a width and height of an implant tooth to be implanted, and including: a body in which a center hole is formed at a center for insertion of a drill blade for inserting an implant and an opened groove is formed at one side of the center portion so as to be easily separated from the drill blade in a state that the drill blade is fixed; and a handle combined to one side of the body.

As another method, "APPARATUS FOR GUIDING IMPLANTS" is disclosed in PCT/GB1993/001214.

The above-stated method relates to an apparatus for guiding an implant, and is provided to guide a drill operation by fixing a device to a patient's body (alveolar bone) by trimming.

However, the abode-stated methods are different than the invention proposed by the present applicant. Specifically, the basic purpose of guiding the operation of the implant is similar to the present invention, but the configuration of the device, which is necessary for the implant operation, is excessively large and the structure and effect of the device are completely different.

In addition, the conventional fixture-inserting apparatus checks only a length and a direction in which the fixture is inserted, thereby deteriorating precision of insertion.

On the other hand, according to the present invention, a direction of an insertion hole is checked first, and then a female screw is formed at an inner wall of the insertion hole according to the checked direction of the insertion hole, which is an effect that cannot be derived from the conventional apparatus.

DISCLOSURE

Technical Problem

The purpose of the present invention is, in a direction checking pin and a guide tap drill kit for insertion of an implant fixture, to provide a package kit that checks whether a direction of an insertion hole that is already formed in an alveolar bone is accurate by using the direction checking pin, and forms a female screw in accordance with the formation direction of the insertion hole at an inner wall of the insertion hole by using the guide tap drill.

Conventionally, a general fixture has an inclined shape and thus when a female screw is formed in an inner wall of an insertion hole, a tap drill that guides a direction cannot be used. Thus, even a well-skilled operator could not avoid occurrence of damage to a peripheral alveolar bone of the insertion hole when he carries out fixture insertion because an error occurs between a formation direction of the insertion hole and an insertion direction of the fixture.

Meanwhile, the present invention provides a package kit that can check a direction of an already-formed insertion hole to insert a fixture for an implant according to a direction of the insertion hole by guiding a screw of the fixture, and form a female screw according to the direction of the insertion hole at an inner wall of the insertion hole.

Technical Solution

In order to achieve such a purpose, the present invention provides a direction checking pint and a guide tap drill for fixture insertion for an implant without causing damage to a peripheral alveolar bone, and thus the direction checking pin formed by combining an endosseous fixing guide 10 and a direction checking pin body 20 is inserted into an already-formed insertion hole and a formation direction of the insertion hole is checked, the direction checking pin body 20 is removed, an insertion hole 30a provided at an end of a tap drill 30 is inserted into a guide rod 12 of the endosseous fixing guide 10, which remains in the insertion hole after a position is determined by the direction checking pin body 20, and then the tap drill 30 enters into the insertion hole while rotating along the endosseous fixing guide 10, and accordingly a screw thread can be formed in the inner wall of the insertion hole in accordance with the formation direction of the insertion hole.

In addition, the tap drill 30 includes a blade portion 31, a drill rod 32, and an insertion hole 30a and enters into the insertion hole while rotating in only one direction, and the blade portion 31 includes a bone cutting portion 31a and an entry direction maintaining portion 31b.

In addition, the endosseous fixing guide 10 includes a fixing head portion 11 fixed to a bottom surface of the insertion hole by contacting the same, and a guide rod 12 that extends to an upper side of the fixing head portion 11.

In addition, the direction checking pin body 20 is formed of an endosseous insertion portion 20a that is formed in the same shape as the insertion hole and an exposure portion 20b exposed to the outside of the insertion hole to check a direction, and an insertion hole 21 that penetrates along a length direction or is concave to a predetermined point is formed in the direction checking pin body 20 such that the guide rod 12 connected to the fixing head portion 11 of the endosseous fixing guide 10 is inserted therein.

The tap drill 30 includes the blade portion 31 of which a screw thread is formed at an exterior diameter thereof, the drill rod 32 extended to an upper side of the blade portion 31, and the insertion hole 30a formed at a center of the blade portion 31 and through which the endosseous fixing guide 10 is inserted.

In addition, the insertion hole 30a to which the endosseous fixing guide 10 is inserted is formed in the tap drill 30, and a diameter C of the insertion hole 30a is the same as a diameter B of the insertion hole 21 of the direction checking pin body 20, while an exterior diameter A of a rod portion of the endosseous fixing guide 10 is the same as or slightly smaller than the diameter B of the insertion hole 21 and the diameter C of the insertion hole 30a of the tap drill 30.

Advantageous Effects

Compared to the direction checking pin and the guide tap drill kit for fixture insertion of the implant according to the present invention, conventionally, there was a problem that a fixture is manually inserted into an already-made insertion hole by an operator (doctor), and thus even though the operator is well skilled, an error always occurs between a direction of the insertion hole and a fixture insertion direction without using a device, thereby causing damage to an alveolar bone at an inner wall of the insertion hole.

Therefore, according to the present invention, a female screw is formed in a direction that precisely matches a formation direction of the insertion hole such that the female screw formed in the inner wall of the insertion hole precisely guides an insertion direction of a fixture, thereby preventing damage to the alveolar bone.

MODE FOR INVENTION

Figure 1A:
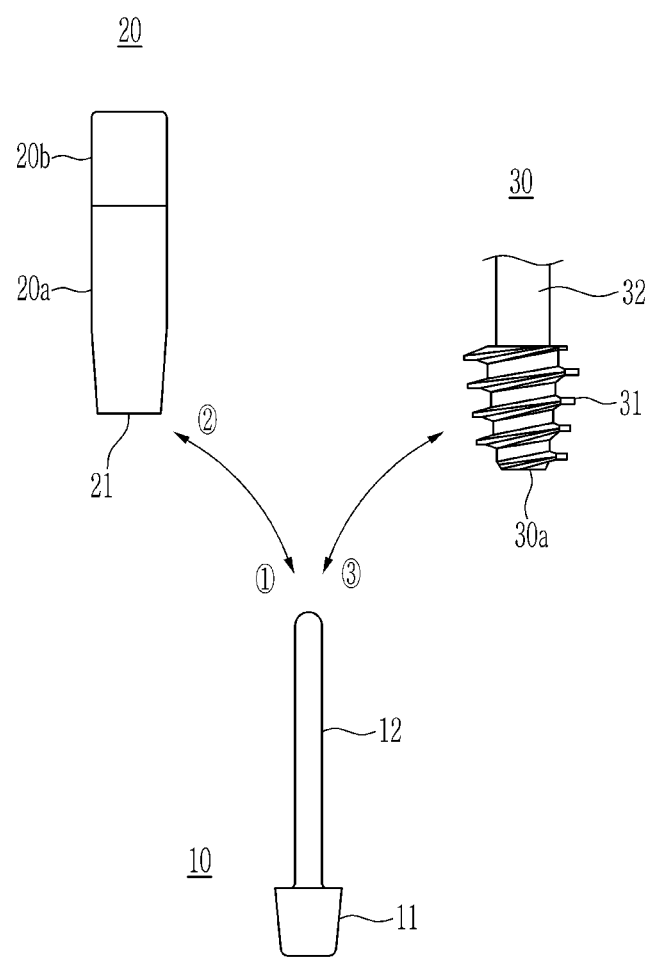
FIG. 1A shows a direction checking pin and a direction checking pin body of a guide tap drill kit for insertion of an implant fixture according to the present invention.

Terms or words used in the specification and claims should not be limited and construed as common or dictionary meanings, and should be construed as meanings and concepts according to the technical spirit of the present invention based on the principle that the inventor can appropriately define the concept of each term for describing the invention in the best way.

The exemplary embodiment described in the present disclosure and the configuration illustrated in the drawings is merely the most preferred embodiment of the present invention, rather than representing all the technical concepts of the present invention, so the present invention is meant to cover all modifications, similarities, and alternatives which are included in the spirit and scope of the present invention at the time of filing of the present invention.

It should be noted that the present invention is not illustrated or is not specifically described with respect to matters not required to reveal the substance of the present invention, that is, a known configuration that can be easily added by a person skilled in the art in advance of describing the present invention with reference to the accompanying drawings.

The present invention relates to a direction checking pin and a guide tap drill kit for insertion of an implant fixture.

Specifically, the present invention relates to a device that forms a female screw in a direction of formation of an insertion hole, which has been already formed, when the female screw is formed at a wall to guide an implant direction of a fixture in the insertion hole by using a tap drill.

Conventionally, an insertion hole for insertion of a fixture is manually formed, and thus even a well-skilled operator (doctor) could not avoid occurrence of damage to a peripheral alveolar bone of the insertion hole when he carries out fixture insertion because an error occurs between a formation direction of the insertion hole and an insertion direction of the fixture.

Accordingly, the present invention relates to a package kit for fixture insertion for an implant by forming an insertion hole according to the intention of the operator and forming a female screw while precisely matching a formation direction of the insertion hole, thereby improving accuracy in an insertion direction of the fixture.

Hereinafter, a direction checking pin and guide tap drill kit for insertion of an implant fixture according to the present invention will be described with reference to the accompanying drawings.

FIG. 1A shows a direction checking pin and a guide tap drill kit for insertion of an implant fixture according to the present invention, and shows the direction checking pin and a direction checking pin body of the guide tap drill kit for insertion of the implant fixture according to the present invention.

Referring to FIG. 1A, the present invention is formed of a package kit that includes an endosseous fixing guide 10, a direction checking pin body 20, and a tap drill 30.

First, the endosseous fixing guide 10 includes a fixing head portion 11 that contacts a bottom surface of implant bone and a guide rod 12 that extends to the upward of the fixing head portion 11.

Next, after the direction checking pin body 20 is combined with the endosseous fixing guide 10 and then inserted into the insertion hole, the direction checking pin body 20 checks a direction and then is separated from the endosseous fixing guide 10 such that only the direction checking pin body 20 can be removed from the alveolar bone.

Figure 1B:
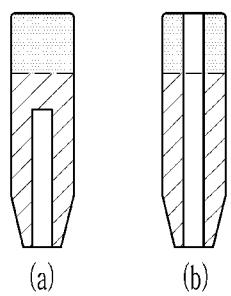
FIG. 1B is provided for description of an exposure portion 20b of the direction checking pin for insertion of the implant fixture and the direction checking pin body of the guide tap drill kit according to the present invention.
Figure 1B:
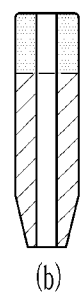
Figure 1B:
Figure 1B:
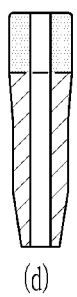
Figure 1B:
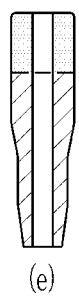
Figure 1B:
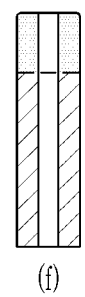

For this purpose, an insertion hole 21 is formed in the direction checking pin body 20 while penetrating the direction checking pin body 20 in a length direction (refer to (b) of FIG. 1B) or is concave to a predetermined point (refer to (a) of FIG. 1B), and thus other portions of the endosseous fixing guide 10, excluding the fixing head portion 11, can be inserted therein.

A shape of a portion inserted into a bone (hereinafter referred to as an in-bone insertion portion 20a of the direction checking pin body 20, referring to (a) and (b) of FIG. 1B, is the same as the shape of the insertion hole, and thus an exterior shape that is straightly formed from the top side toward a lower direction and then inclined from a predetermined point can be formed.

However, this is not restrictive, and the entire endosseous insertion portion 20a may be inclined as shown in (c) of FIG. 1B, an inclined portion and a straight line portion may be repeatedly shown in (d), a straight line portion and an inclined portion may be repeatedly shown in (e) be straight lined, and the entire exterior shape may be straight lined as shown in (f).

In addition, as shown in (a), (b), and (c) of FIG. 1B, the exposure portion may be larger than or smaller than the endosseous insertion portion 20a, or may be the same size as the endosseous insertion portion 20a.

The tap drill 30 is combined to the endosseous fixing guide 10 that is separated from the direction checking pin body 20 and forms a screw thread at an inner wall of the insertion hole by performing tap drilling.

Such a tap drill 30 includes a blade portion 31 of which a screw thread is formed at an exterior diameter thereof, a drill rod 32 extended to an upper side of the blade portion 31, and an insertion hole 30a through which the endosseous fixing guide 10 is inserted, and bone cutting portions 31a and an entering direction maintaining portion 31b are formed in the blade portion 31.

In this case, the insertion hole 30a formed in the tap drill 30 may have a diameter C, which is the same as a diameter B of the insertion hole 21 of the direction checking pin body 20, such that the tap drill 30 can be inserted into the guide rod 12 of the endosseous fixing guide 10.

In this case, an exterior diameter A of a rod portion of the endosseous fixing guide 10 may be smaller than the diameter B of the insertion hole 21 of the direction checking pin body 20 and the diameter C of the insertion hole 30a of the tap drill 30.

This will be described with reference to FIG. 2.

Figure 2:
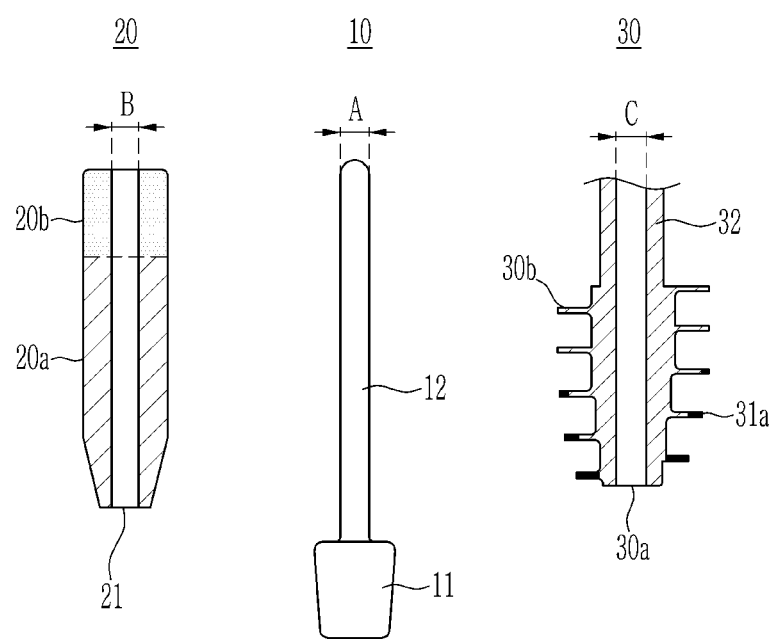
FIG. 2 is provided for additional description of the direction checking pin for inserting the implant fixture and the direction checking pin body of the guide tap drill kit according to the present invention.

FIG. 2 is provided for additional description of the direction checking pin and the guide tap drill kit for inserting the implant fixture according to the present invention.

An operator fits the insertion hole 30a of the tap drill 30 to the endosseous fixing guide 10 and maintains a direction to insert the tap drill 30 into the insertion hole insertion hole 30a while rotating the tap drill 30.

In this case, the insertion hole 30a included in the tap drill 30 may or may not be penetrated.

In addition, depending on designs, a flexible material such as silicon, which is harmless to a human body, may be formed with a stacked structure at the end of the tap drill 30 for the purpose of alleviating pain of a patient. Thus, when the tap drill 30 touches the endosseous fixing guide 10, less vibration is generated, thereby reducing the patient's pain.

Meanwhile, depending on another design condition, a female screw thread or a male screw thread is formed at a lower exterior surface of the guide rod 12 of the endosseous fixing guide 10, a female screw thread or a male screw thread is formed at a lower interior surface of the insertion hole 30a of the tap drill 30, and thus when the tap drill 30 is completely inserted into the endosseous fixing guide 10, the tap drill 30 and the endosseous fixing guide 10 are simultaneously combined.

Accordingly, it is advantageous because when the tap drill 30 is removed from the insertion hole, the endosseous fixing guide 10 can be removed together therewith.

In addition, referring to FIG. 2, the exterior diameter A of the guide rod 12 of the endosseous fixing guide 10, the interior diameter B of the insertion hole 21 of the pin body 20, and the interior diameter C of the insertion hole 30a of the tap drill 30 are shown.

In this case, A is set to be smaller than or equal to B such that the guide rod 12 of the endosseous fixing guide 10 can be smoothly inserted into the insertion hole 21.

In addition, A is set to be smaller than C, and thus the endosseous fixing guide 10 can be smoothly inserted into the insertion hole 30a of the guide rod 12.

With such a structure, the fixing head portion 11 of the endosseous fixing guide 10 may have a diameter that is larger than a diameter of the end of the direction checking pin body 20, and thus, when the endosseous fixing guide 10 is inserted into the insertion hole, the fixing head portion 11 is forcedly fitted by using elasticity of the alveolar bone and, in this chase, when the direction checking pin body 20 is separated from the endosseous fixing guide 10, the separation can be easily carried out without causing a direction change of the endosseous fixing guide 10.

Now, the blade portion 31 will be described with reference to FIG. 4A and FIG. 4B.

Figure 4A:
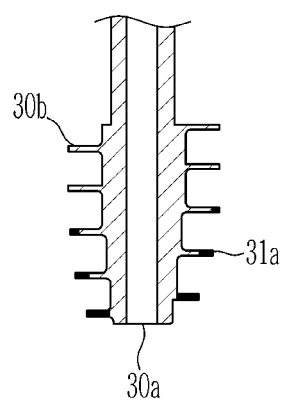
FIG. 4A is an enlarged view of a case that the entire blade portion of the tap drill is a bone cutting portion in the direction checking pin and the guide tap drill kit for insertion of the implant fixture according to the present invention.
Figure 4A:
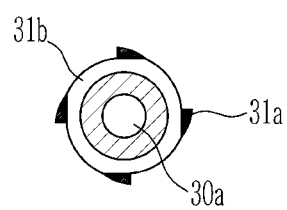
Figure 4B:
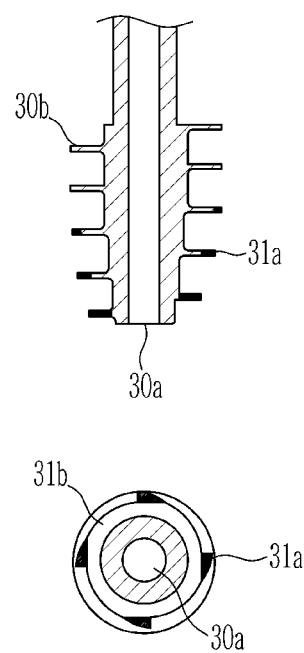
FIG. 4B is an enlarged view of a case that a bone cutting portion is partially formed in the blade portion of the tap drill.
Figure 5:
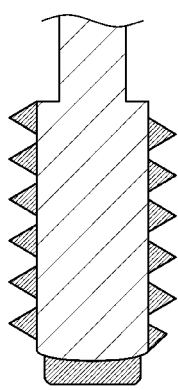
FIG. 5 is an enlarged view of a blade portion of a commonly used tap drill compared to the present invention.
Figure 5:
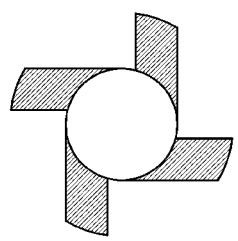
Figure 6:
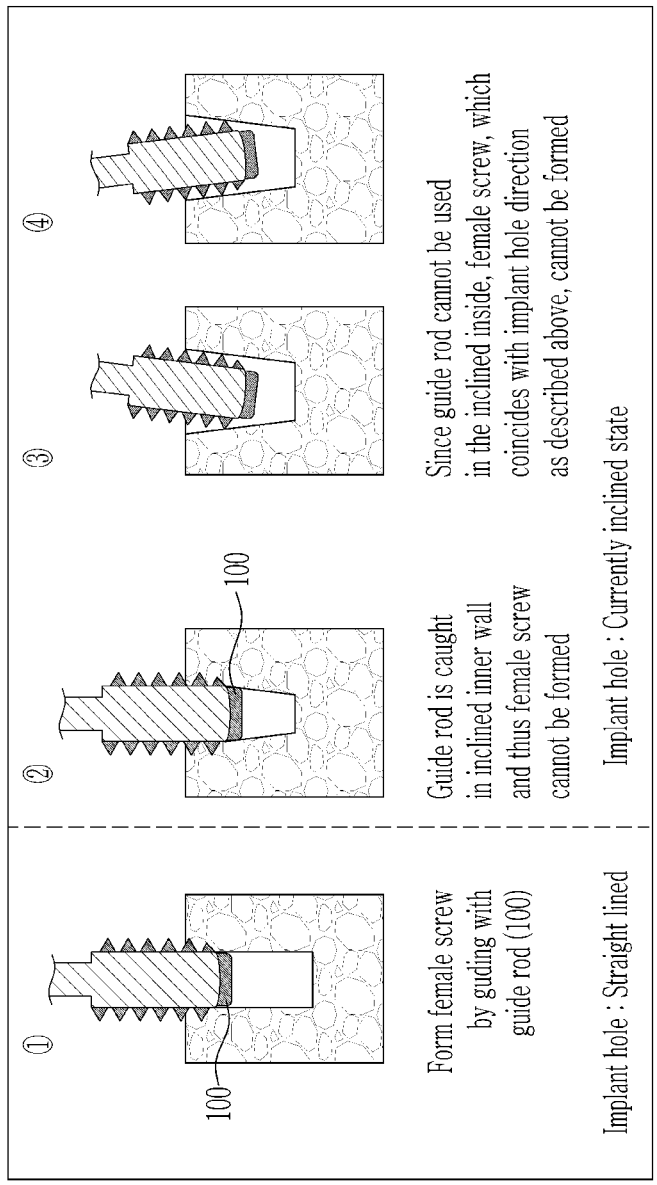
FIG. 6 is additionally provided for description of a problem of a conventional art.

FIG. 4A and FIG. 4B are enlarged view of the direction checking pin for inserting of the implant fixture and the blade portion of the tap drill in the guide tap drill kit according to the present invention.

Referring to FIG. 4A and FIG. 4B, the upper side of each drawing is a perspective view of the blade portion 31, and the lower side of each drawing illustrates the tap drill 30 viewed from an end direction where the blade portion 31 is formed. Referring to the lower side of the drawing, the blade portion 31 may be provided in the shape of a pinwheel.

Referring to FIG. 4A and FIG. 4B, the blade portion 31 of the tap drill 30 will now be described in detail.

As shown in FIG. 4, the blade portion 31 has a shape in which the diameter of the screw increases from the lower side to the upper side. In this case, screw are formed from the initial starting screw point, and then a screw is formed again at a predetermined point with an increased width and another screw is formed at another point with a more increased width, and such a process is repeated.

In this case, an area where the screw is formed becomes a bone cutting portion 31a where cutting blades are formed to cut the alveolar bone, and other areas become an entry direction maintaining portion 31b that helps the bone cutting portion 31a to be inserted into the insertion hole along a constant direction.

In such a structure, a boundary of an entry direction maintaining portion 31b at an inner side of a bone cutting portion 31a at an n-th layer should have a larger diameter than the outermost end of a bone cutting portion 31a at an (n−1)th layer in the blade portion 31.

This is because when the bone cutting portion 31a of the upper layer again passes the bone cutting portion 31a that the upper layer has passed, the patient's pain is increased, and a cut portion is cut again so that the screw thread for fixture the implant may not correctly placed.

Thus, the bone cutting portion 31a in the lower layer does not again pass a place that the bone cutting portion 31a in the upper layer passed, only the entry direction maintaining portion 31b in the upper layer passes an area of the alveolar bone, cut by the lower bone cutting portion 31, and the bone cutting portion 31a in the upper layer should be used for the purpose of widening a cutting portion.

Meanwhile, as shown in FIG. 4, the insertion hole 30a is formed in the tap drill 30 and the insertion hole 30a is fully hollow from one end to the opposite end such that remnants of the alveolar bone and blood generated during the cutting operation can be discharged to the outside without being left in the insertion hole.

However, depending on design conditions, groove portions may be formed at regular intervals along an external circumference of the blade portion 31 of the tap drill 30. Such a screw thread structure enables the screw thread to be easily formed at an inner wall of the insertion hole, and the screw thread can be easily removed from the insertion hole by turning the tap drill 30 in the opposite direction.

Hereinafter, an implant fixture inserting process carried out by using the above-described direction checking pin and the guide tap drill kit for inserting the implant fixture will be described.

Figure 3:
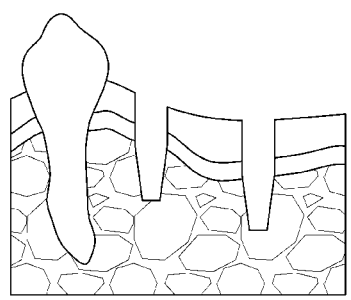
FIG. 3 exemplarily shows a process for carrying out implantation by using the direction checking pin for insertion of the implant fixture and the direction checking pin body of the guide tap drill kit according to the present invention.
Figure 3:
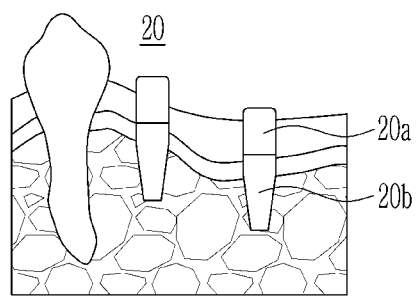
Figure 3:
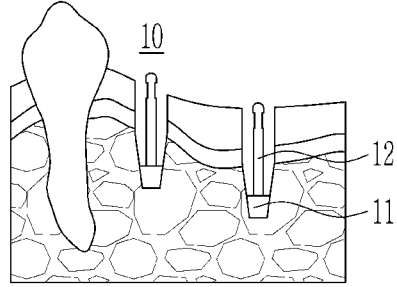
Figure 3:
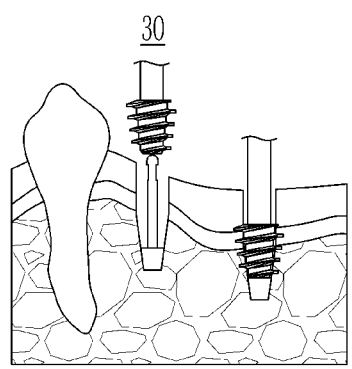
Figure 3:
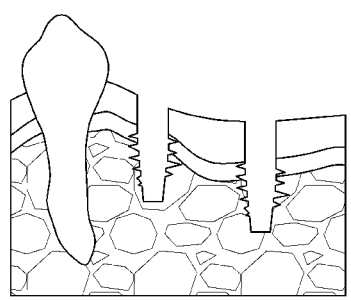
Figure 3:
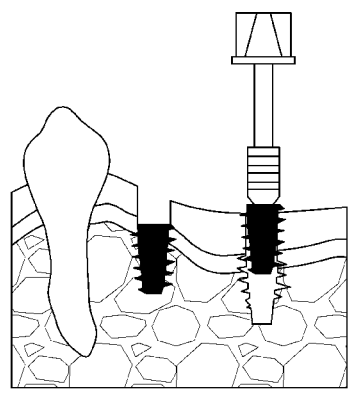

FIG. 3 exemplarily illustrates a process for carrying out an implant by using the direction checking pin and the guide tap drill kit for insertion of an implant fixture according to the present invention.

Referring to FIG. 2 and FIG. 3,

① an insertion hole is formed at an alveolar bone from which a tooth is removed. In this case, the insertion hole is formed by using a conventional implant drill, and therefore no further detailed description will be provided.

② The endosseous fixing guide 10 and the direction checking pin body 20 are combined and then inserted into the insertion hole, and then pressure is slightly applied thereto.

③ After checking the direction of the insertion hole, only the direction checking pin body 20 is separated from the insertion hole such that only the endosseous fixing guide 10 remains in the insertion hole.

④ The insertion hole 30a of the tap drill 30 is inserted into the endosseous fixing guide 10 and then rotated to enter into the endosseous fixing guide 10, and then a screw thread is formed at an inner wall of the insertion hole. In this case, the tap drilling is guided by the endosseous fixing guide 10 and thus the tap dripping can be easily carried out in accordance with a direction of the insertion hole formed according to the intention of the operator or in the direction in which the insertion hole is formed.

⑤ The tap drill 30 and the endosseous fixing guide 10 are removed from the insertion hole.

⑥ The fixture is implanted by forming a screw thread in the female screw formed in the inner wall of the insertion hole.

It is apparent that the present invention is not limited to the configuration of the drawings, as described above with reference to the drawings, only the main points of the present invention are described, and various designs can be made within the technical scope thereof.

The invention claimed is:

1. A direction checking pin and a guide tap drill kit for insertion of a fixture for a dental implant, comprising:
   an endosseous fixing guide (10);
   a direction checking pin body (20); and
   a guide tap drill (30),
   wherein the endosseous fixing guide (10) and the direction checking pin body (20) are configured to be combined and then inserted into an already-formed insertion hole in an alveolar bone and only the direction checking pin body (20) is removed after checking a direction of the insertion hole, and the guide tap drill (30) configured to be inserted on the endosseous fixing guide (10) remaining in the insertion hole and then rotated so as to enter into the insertion hole such that a screw thread is formed in accordance with the direction of the insertion hole at an inner wall of the insertion hole by the guide tap drill (30).

2. The direction checking pin and the guide tap drill kit for insertion of the dental implant fixture of claim 1, wherein the endosseous fixing guide (10) comprises a fixing head portion (11) that is configured to contact a bottom surface of the insertion hole and a guide rod (12) that extends upward from the fixing head portion (11).

3. The direction checking pin and the guide tap drill kit for insertion of the dental implant fixture of claim 2,
   wherein the direction checking pin body (20) comprises an endosseous insertion portion (20a) insertable into the insertion hole and an exposure portion (20b) that is configured to be disposed at the outside of the insertion hole to indicate a direction of the insertion hole, and
   the direction checking pin body (20) has a hole (21) that is penetrating along a length direction inside the direction checking pin body (20) or is concave to a predetermined point and thus other parts of the endosseous fixing guide (10), excluding the fixing head portion (11), are insertable into the hole (21).

4. The direction checking pin and the guide tap kit for insertion of the dental implant fixture of claim 2, wherein the guide tap drill (30) comprises a blade portion (31) where screw threads are formed at an exterior diameter and a drill rod (32) extending upwards from the blade portion (31).

5. The direction checking pin and the guide tap drill kit for insertion of the dental implant fixture of claim 3, wherein an insertion hole (30a) of the guide tap drill into which the endosseous fixing guide (10) is insertable is formed in the guide tap drill (30), and
   a diameter (C) of the insertion hole (30a) of the guide tap drill is the same as a diameter (B) of the hole (21) of the direction checking pin body (20), while
   an exterior diameter (A) of the guide rod of the endosseous fixing guide (10) is the same as or slightly smaller than the diameter (B) of the hole of the direction checking pin body and the diameter (C) of the insertion hole (30a) of the guide tap drill (30).

6. The direction checking pin and the guide tap drill kit for insertion of the dental implant fixture of claim 4, wherein the blade portion (31) includes a bone cutting portion (31a) configured to cut the alveolar bone and an entry direction maintaining portion (31b) that maintains an entry direction.

\* \* \* \* \*